United States Patent
Rose (10) Patent No.: US 9,855,462 B2
(45) Date of Patent: Jan. 2, 2018

(54) KEGEL HEALTH SYSTEM

(71) Applicant: Kalikha Inc., Los Angeles, CA (US)

(72) Inventor: Julia Rose, Los Angeles, CA (US)

(73) Assignee: Kalikha Inc., Los Angeles, CA (US)

(*) Notice: Subject to any disclaimer, the term of this patent is extended or adjusted under 35 U.S.C. 154(b) by 0 days.

(21) Appl. No.: 15/079,807

(22) Filed: Mar. 24, 2016

(65) Prior Publication Data

US 2016/0279469 A1  Sep. 29, 2016

Related U.S. Application Data

(60) Provisional application No. 62/137,334, filed on Mar. 24, 2015.

(51) Int. Cl.
| A63B 23/20 | (2006.01) |
| A63B 24/00 | (2006.01) |

(Continued)

(52) U.S. Cl.
CPC ............ *A63B 23/20* (2013.01); *A61B 5/1107* (2013.01); *A61B 5/4356* (2013.01); *A61B 5/486* (2013.01); *A63B 21/0004* (2013.01); *A63B 71/0622* (2013.01); *A61H 19/44* (2013.01); *A61H 2201/0188* (2013.01); *A61H 2201/1207* (2013.01); *A61H 2201/1261* (2013.01); *A61H 2201/1628* (2013.01);

(Continued)

(58) Field of Classification Search
CPC ..... A63B 23/20; A63B 2220/56; A61B 5/227; A61N 1/36007
USPC ........................................................ 600/591
See application file for complete search history.

(56) References Cited

U.S. PATENT DOCUMENTS

| 5,733,230 A | * | 3/1998 | Sawchuck | ............... | A63B 23/20 |
| | | | | | 482/111 |
| 6,428,467 B1 | * | 8/2002 | Benderev | ............... | A61F 2/0009 |
| | | | | | 128/DIG. 25 |

(Continued)

FOREIGN PATENT DOCUMENTS

| CA | 2684004 A1 | 6/2006 |
| CA | 2591401 A1 | 6/2007 |

(Continued)

OTHER PUBLICATIONS http://www.magicsmotion.com/Twins/, Magic Motion, China.

(Continued)

*Primary Examiner* — Sean Dougherty
*Assistant Examiner* — Patrick Fernandes
(74) *Attorney, Agent, or Firm* — Robert Crownover (57) ABSTRACT

A method and apparatus for a Kegel health system can include: inserting an insertable body into a user, the insertable body connected to a tail outside of the user, the insertable body including a bulbous body coupled to a connecting body, the bulbous body including a control unit, the connecting body coupled to the tail, and the connecting body including sensors; sensing sensor data with the sensors, the sensor data indicating the presence of contractions from a pelvic floor muscle of the user; providing feedback to the user with graphics and written information displayed on an external device, the graphics and the written information indicating attributes of the contractions from the pelvic floor muscle.

17 Claims, 5 Drawing Sheets

(51) Int. Cl.
    A63B 71/06    (2006.01)
    A61B 5/00     (2006.01)
    A63B 21/00    (2006.01)
    A61B 5/11     (2006.01)
    H04M 1/725    (2006.01)
    A61H 19/00    (2006.01)

(52) U.S. Cl.
    CPC ........... A61H 2201/1635 (2013.01); A61H
        2201/501 (2013.01); A61H 2201/5012
        (2013.01); A61H 2201/5015 (2013.01); A61H
        2201/5043 (2013.01); A61H 2201/5048
        (2013.01); A61H 2201/5071 (2013.01); A61H
        2201/5079 (2013.01); A63B 24/0062
        (2013.01); A63B 2071/065 (2013.01); A63B
        2071/0625 (2013.01); A63B 2071/0655
        (2013.01); A63B 2220/17 (2013.01); A63B
        2220/30 (2013.01); A63B 2220/56 (2013.01);
        A63B 2220/64 (2013.01); A63B 2225/02
        (2013.01); A63B 2225/50 (2013.01); H04M
        1/7253 (2013.01)

(56)         References Cited

U.S. PATENT DOCUMENTS 6,468,232  B1 * 10/2002  Ashton-Miller ....... A61B 5/227
                                                       600/591
    2003/0036464 A1    2/2003  Zavilevich
    2003/0220589 A1 * 11/2003  Leivseth ............... A61B 5/227
                                                       600/591
    2006/0036188 A1 *  2/2006  Hoffman ............... A61B 5/0002
                                                       600/591
    2010/0087757 A1    4/2010  Hoffman et al.
    2014/0174174 A1 *  6/2014  Uehara ................. A61B 5/227
                                                       73/379.01

FOREIGN PATENT DOCUMENTS

CA         2678298   A1      3/2011
    CA         2841804   A1      1/2013
    CN       203953665   U  *   11/2014
    CN        104436544   A      3/2015
    ES   WO 2014013118   A9 *    3/2014    .......... A61B 5/04862
    KR      20150105607   A      9/2015
    WO         2005049151 A1     6/2005
    WO         2014127526 A1     8/2014
    WO         2016042310 A1     3/2016
    WO         2016067023 A1     5/2016

OTHER PUBLICATIONS http://www.minnalife.com/products/kgoal, kGoal by Minna Life, San Francisco.
https://www.kickstarter.com/projects/2091647642/skea-smart-kegel-exercise-aid, SKEA, China.
https://www.chiaro.co.uk/page/about-us, Elvie by Chiaro, UK.

* cited by examiner

KEGEL HEALTH SYSTEM

CROSS-REFERENCE TO RELATED APPLICATIONS

This claims priority benefit to all common subject matter of U.S. Provisional Patent Application No. 62/137,334 filed Mar. 24, 2015. The content of this application is incorporated herein by reference.

TECHNICAL FIELD

This disclosure relates to systems of maintaining and improving musculature health, more particularly to a system for training and tracking the health of the pelvic floor muscle.

BACKGROUND

Urinary incontinence in women is a condition involving the involuntary leakage of urine. This condition is caused by the weakening of the pelvic floor muscles, also known as the Kegel muscle, that aid in controlling urination. Urinary incontinence may be caused by pregnancy and childbirth, menopause, long term physical exertion, neurological injury, birth defects, and obesity in women of all ages, but is most prevalent in women over 60 and in the months following pregnancy and child birth.

To combat urinary incontinence, Kegel muscle training and strengthening exercise methods have proven beneficial. These exercises serve to develop stronger reflexive contractions following a rise in intra-abdominal pressure. Kegel exercises have also been cited in strengthening pelvic floor muscles for easier pregnancy and childbirth, increasing pleasure during sexual activity, treating conditions such as vaginosis, and helping to prevent organ prolapse. However, it can be difficult to perform these exercises because they are challenging and easily done incorrectly. Moreover, there is no effective way to teach proper form, track a pelvic floor muscle contraction, measure exercise results and provide more advanced exercise levels upon improvement.

Several prior developments have been set forth to aid women with their Kegel exercises. Some involve electrical stimulation of the Kegel muscles, some involve inserting weighted objects in to the vaginal canal to force the Kegel muscles to contract to hold them in, and some require the user to use their hands to manually manipulate a device during exercises. A few devices provide air pressure gauges that measure muscle contraction strength and others assume a physical vibration can elicit muscle response.

While using some of these devices may be more effective than trying to perform Kegel exercises alone, they are inconvenient and complicated, while others might provide negative or harmful results. In light of the current developments, there still does not exist a good method for teaching a woman to do the exercise correctly and effectively, measuring and charting progress, customizing exercise programs to a single user, evaluating exercise results, or engaging the user to exercise for a significant amount of time.

Solutions have been long sought but prior developments have not taught or suggested any complete solutions, and solutions to these problems have long eluded those skilled in the art. Thus there remains a considerable need for devices and methods that can teach proper form, measure exercise results and enable more advanced exercise levels upon improvement.

SUMMARY

A Kegel health systems and methods, ensuring proper form, measuring exercise results and enabling more advanced exercise levels upon improvement, are disclosed. The Kegel system and methods can include: inserting an insertable body into a user, the insertable body connected to a tail outside of the user, the insertable body including a bulbous body coupled to a connecting body, the bulbous body including a control unit, the connecting body coupled to the tail, and the connecting body including sensors; sensing sensor data with the sensors, the sensor data indicating the presence of contractions from a pelvic floor muscle of the user; providing feedback to the user with graphics and written information displayed on an external device, the graphics and the written information indicating attributes of the contractions from the pelvic floor muscle.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The Kegel system is illustrated in the figures of the accompanying drawings which are meant to be exemplary and not limiting, in which like reference numerals are intended to refer to like components, and in which.

DETAILED DESCRIPTION

In the following description, reference is made to the accompanying drawings that form a part hereof, and in which are shown by way of illustration, embodiments in which the Kegel system may be practiced. It is to be understood that other embodiments may be utilized and structural changes may be made without departing from the scope of the Kegel system.

When features, aspects, or embodiments of the Kegel system are described in terms of steps of a process, an operation, a control flow, or a flow chart, it is to be understood that the steps can be combined, executed in a different order, deleted, or include additional steps without departing from the Kegel system as described herein. When functions, acts, steps, or processes are described as executed by units of the Kegel system 100, it is to be understood that the components of the units can perform the action.

The Kegel system is described in sufficient detail to enable those skilled in the art to make and use the Kegel system and provide numerous specific details to give a thorough understanding of the Kegel system; however, it will be apparent that the Kegel system may be practiced without these specific details.

In order to avoid obscuring the Kegel system, some well-known system configurations are not disclosed in detail. Likewise, the drawings showing embodiments of the system are semi-diagrammatic and not to scale and, particularly, some of the dimensions are for the clarity of presentation and are shown greatly exaggerated in the drawing FIGs. As used herein, the term coupled means a physical connection.

Figure 1:
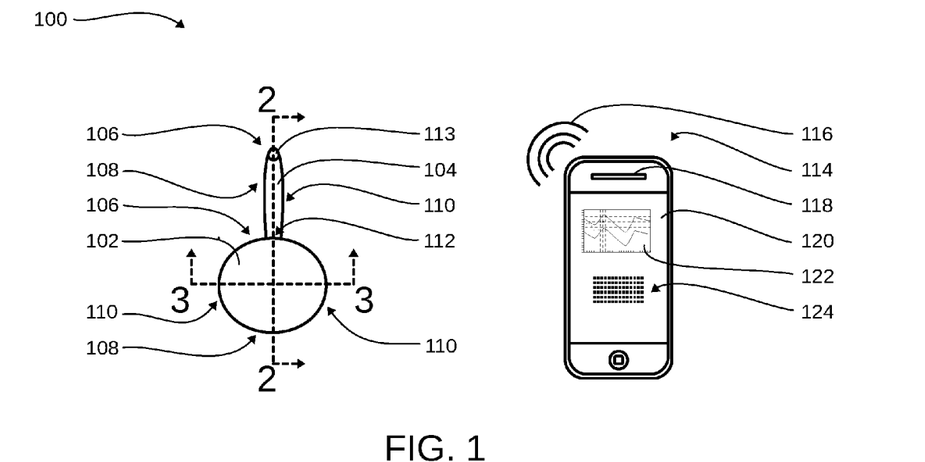
FIG. 1 is a top view of the Kegel health system in a first embodiment.

Referring now to FIG. 1, therein is shown a top view of the Kegel system 100 in a first embodiment. The Kegel system 100 is shown having an insertable body 102 and a tail 104.

It is contemplated that the insertable body 102 and the tail 104 can include a medical grade silicone outer sleeve encasing a housing, a chassis, and electro-mechanical components, as described below. The insertable body 102 and the tail 104 are shown to include front portions 106, back portions 108, lateral portions 110, and medial portions 112.

The medial portions 112 of the insertable body 102 and the tail 104 can be between the lateral portions 110. The tail 104 is shown extending away from the front portion 106 of the insertable body 102 with the back portion 108 of the tail 104 facing the front portion 106 of the insertable body 102. The lateral portions 110 can be arranged perpendicularly to the front portions 106 and the back portions 108 on both the tail 104 and the insertable body 102.

The Kegel system 100 is further shown including an external device 114. The external device 114 is contemplated to be a cellular phone, a tablet computer, a laptop, or other computing device. The two components of the Kegel system 100 are shown communicating with a wireless signal 116, which can propagate therebetween.

It is alternatively contemplated that the Kegel system 100 could communicate or charge with a physical wire connection. For example it is contemplated that a Universal Serial Bus Cable could be used to connect and communicate between the insertable body 102 and the external device 114.

The external device 114 is depicted having interface components such as speakers 118 and a display 120. The display 120 can include graphics 122 such as a game along with written information 124 including statistics, scores, time limits, and instructions.

Figure 2:
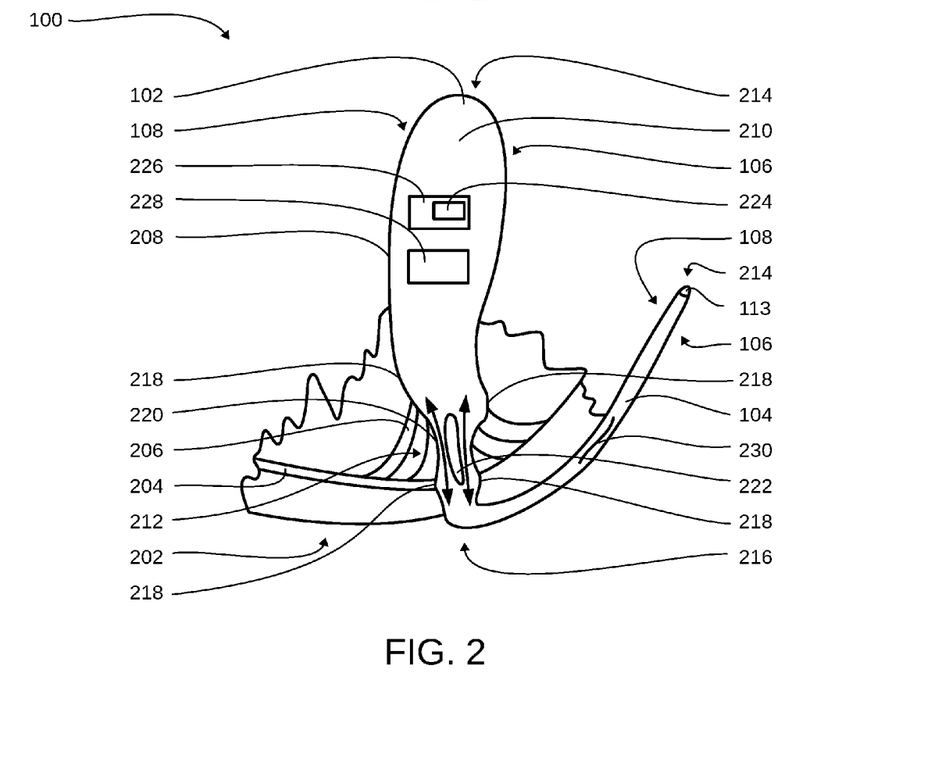
FIG. 2 is a cross-sectional view of the Kegel health system along the line 2-2 of FIG. 1 in an inserted phase of operation.

Referring now to FIG. 2, therein is shown a cross-sectional view of the Kegel system 100 along the line 2-2 of FIG. 1 in an inserted phase of operation. The Kegel system 100 is shown inserted into a user 202 and extending above and below a pelvic floor 204 and pelvic floor muscles 206 of the user 202. As used herein, the term "Kegel" and "Kegel muscles" refers to the pelvic floor muscle 206.

The pelvic floor muscles 206 are depicted surrounding the insertable body 102 of the Kegel system 100. Further, the pelvic floor muscles 206 are depicted in direct contact with a surface 208 of the insertable body 102.

The insertable body 102 can be comprised of two portions including a bulbous body 210 and a connecting body 212. The bulbous body 210 is depicted near a top portion 214 of the insertable body 102 while the connecting body 212 is depicted near a bottom portion 216 of the insertable body 102.

The bulbous body 210 can extend downward from the top portion 214 of the insertable body 102 and terminate at the connecting body 212. The connecting body 212 can extend upward from the bottom portion 216 of the insertable body 102 and terminate at the bulbous body 210.

The tail 104 can extend from the bottom portion 216 of the insertable body 102 and can be in direct contact with the connecting body 212. The tail 104 is depicted extending outward away from the front portion 106 of the insertable body 102 and external to the user 202.

It is contemplated that the tail 104 would remain external to the user 202 while in use. The bottom portions 216 of the connecting body 212 and the tail 104 can form an L shape to anchor the Kegel system 100 in the proper position relative to the pelvic floor muscles 206 and the pelvic floor 204 of the user 202.

The tail 104 can extend laterally from the connecting body 212 and curve upward near the top portion 214 of the tail 104 so that the top portion 214 of the tail 104 extends at roughly a forty-five degree angle away from the connecting body 212.

The insertable body 102 is further depicted including anchor protrusions 218. The anchor protrusions 218 can be located on the insertable body 102 above and below the pelvic floor muscles 206.

The anchor protrusions 218 can extend outward from the connecting body 212 and form concave recesses 220 within the connecting body 212 that extend vertically between the anchor protrusions 218. The anchor protrusions 218 and the concave recesses 220 can be formed within the surface 208 of the connecting body 212.

The bulbous body 210 can taper down from the top portion 214 to the anchor protrusions 218. The bulbous body 210 can be narrower near the anchor protrusions 218 than the anchor protrusions 218.

The top and bottom of the pelvic floor muscles 206 can be in direct contact with the anchor protrusions 218. The pelvic floor muscles 206 can further be in direct contact with the concave recesses 220 during use.

It is contemplated that when the pelvic floor muscles 206 contract, the pelvic floor muscles 206 will thicken and force the concave recesses 220 inward towards each other. The contraction of the pelvic floor muscles 206 will also result in an elongation of the concave recesses 220 as the anchor protrusions 218 are forced apart.

Within the connecting body 212, sensors 222 can be located. The sensors 222 can be an electro-mechanical strain-gauge sensor array, an array of resistive sensors, or a combination thereof. It is contemplated that the sensors 222 can be located entirely within the connecting body 212 or can extend from within the connecting body 212 partially into the bulbous body 210.

As depicted, the sensors 222 can be arranged within the insertable body 102 and is depicted located centrally within the insertable body 102. It is contemplated that the sensors 222 can also be located laterally near the surface 208 of the insertable body 102. The sensors 222 can detect the contractions of the pelvic floor muscles 206 in many ways.

The sensors 222 can detect the separation of the anchor protrusions 218 elongating the concave recesses 220. The sensors 222 can further detect the separation between the connecting body 212, the tail 104, and the bulbous body 210 during a contraction of the pelvic floor muscles 206.

The sensors 222 can further detect movement of the pelvic floor muscles 206 on the surface 208 of the insertable body 102 when the sensors 222 are located on or just under the surface 208 of the insertable body 102. The sensors 222 can further detect pressure exerted on the insertable body 102 during the contractions of the pelvic floor muscles 206. The sensors 222 can yet further detect the amount of surface contact between the pelvic floor muscles 206 and the surface 208 of the insertable body 102 when the sensors 222 are located on or just under the surface 208 of the insertable body 102.

The sensors 222 can output sensor data 224 to a control unit 226. The sensor data 224 can be data sensed during and in between contractions of the pelvic floor muscles 206.

The sensors 222 detect and digitize the evenness, pressure, frequency, number, intensity, speed, and direction of the contractions of the pelvic floor muscles 206. The sensors 222 can further determine whether the pelvic floor muscles 206 are contracting an even manner, that is: to what degree the pelvic floor muscles 206 thicken at various points around the connecting body 212.

The control unit 226 can be encased and located within the bulbous body 210. The control unit 226 can be implemented in a number of different manners. For example the control unit 226 can be a printed circuit board assembly having a master control unit, a power management IC, a radio transceiver, non-volatile computer readable memory, motion or positional sensors, charging components, and battery protection circuits.

The master control unit and the power management IC can be implemented as a processor, an embedded processor, a microprocessor, a hardware control logic, a hardware finite state machine, a digital signal processor, or a combination thereof. The radio transceiver can be implemented as a blue tooth radio.

The non-volatile computer readable memory can be implemented as random access memory, flash memory, or disk storage. The positional or motion sensors can be implemented as accelerometers and magnetometers.

The charging components are contemplated to include inductive charging components coupled to a battery within the bulbous body 210. The control unit 226 can process the sensor data 224 from the sensors 222, can store the sensor data 224, and can communicate the sensor data 224 or processed sensor data 224.

The control unit 226 can further be used to control a biofeedback unit 228. The biofeedback unit 228 can be implemented to include a vibration motor or alternatively as a mechanism to expand and contract portions of the insertable body 102. The biofeedback unit 228 can provide feedback in the form of vibrations to the user 202 based on the evenness, pressure, frequency, number, intensity, speed, and direction of contractions of the pelvic floor muscles 206.

It is contemplated that the biofeedback unit 228 can be located in the bulbous body 210, the connecting body 212, or even in the tail 104. The control unit 226, the sensors 222, and the biofeedback unit 228 can be coupled with coaxial cables and coaxial connections therebetween. The control unit 226 can further be coupled to antennas 230 positioned within the tail 104.

The control unit 226 can be coupled to the antennas 230 with the coaxial connections and the coaxial cable. The antennas 230 can be encased within the tail 104 external to the user 202.

The antennas 230 can transmit the sensor data 224 to the external device 114 of FIG. 1. The antennas 230 can also receive information from the external device 114.

For example it is contemplated that some of the processing of the sensor data 224 can be accomplished by the external device 114 to save power. When the sensor data 224 is processed by the external device 114, the external device 114 can provide instructions about how the biofeedback unit 228 should provide feedback including frequency, intensity, and pattern of vibrations from the biofeedback unit 228 to the user 202.

It is further contemplated that the biofeedback unit 228 can be instructed by the external device 114 to synchronize the biofeedback to the user 202 with the graphics 122 of FIG. 1 and written information 124 of FIG. 1 displayed to the user 202 on the display 120 of FIG. 1. It is further contemplated that the biofeedback unit 228 can be synchronized to deliver biofeedback to audio feedback of the speakers 118 of FIG. 1.

Figure 3:
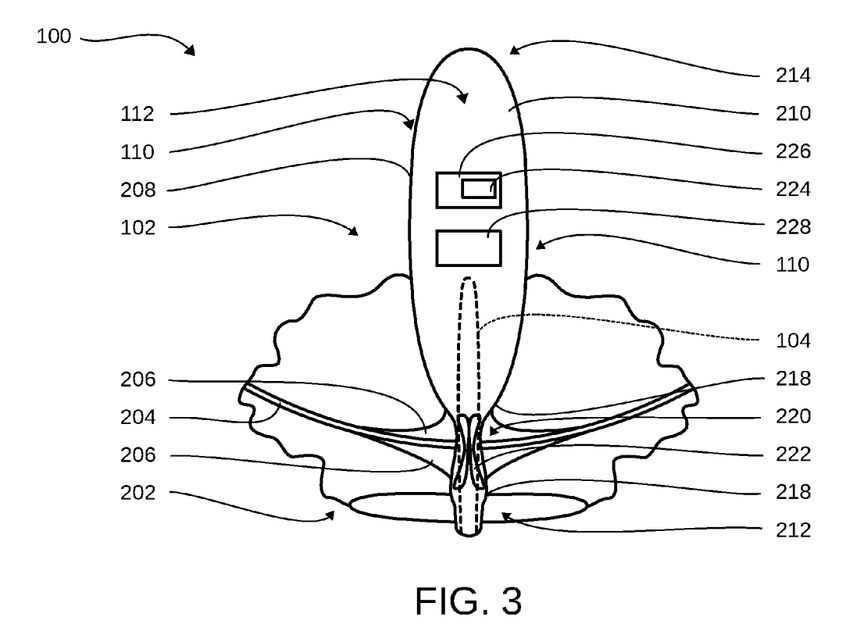
FIG. 3 is a cross-sectional view of the Kegel health system along the line 3-3 of FIG. 1 in an inserted phase of operation.

Referring now to FIG. 3, therein is shown a cross-sectional view of the Kegel system 100 along the line 3-3 of FIG. 1 in an inserted phase of operation. The Kegel system 100 is shown inserted into the user 202 and extending above and below the pelvic floor 204 and the pelvic floor muscles 206 of the user 202.

The pelvic floor muscles 206 are depicted surrounding the insertable body 102 of the Kegel system 100. Further, the pelvic floor muscles 206 are depicted in direct contact with the surface 208 of the insertable body 102.

The bulbous body 210 can extend three and one quarter inches from the connecting body 212 to the top portion 214 of the insertable body 102. The bulbous body 210 can be a bulbous shape when viewed from the cross-sectional line 3-3.

The insertable body 102 is further depicted including the anchor protrusions 218. The anchor protrusions 218 can be located on the lateral portions 110 of the insertable body 102 and can be positioned within the user 202 above and below the pelvic floor muscles 206.

The anchor protrusions 218 can extend laterally outward away from the medial portions 112 of the connecting body 212 and can form the concave recesses 220 within the connecting body 212. The concave recesses 220 can extend vertically between the anchor protrusions 218.

The anchor protrusions 218 and the concave recesses 220 can be formed within the surface 208 of the connecting body 212. The surface 208 of the bulbous body 210 is shown with a smooth rounded transition from the top portion 214 of the bulbous body 210 to the anchor protrusions 218 of the connecting body 212.

The bulbous body 210 can taper down from the top portion 214 to the anchor protrusions 218. The bulbous body 210 can be narrower than or similar size to the anchor protrusions 218 near the anchor protrusions 218.

The top and bottom of the pelvic floor muscles 206 can be in direct contact with the anchor protrusions 218. The pelvic floor muscles 206 can further be in direct contact with the concave recesses 220 during use.

It is contemplated that when the pelvic floor muscles 206 contract, the pelvic floor muscles 206 will thicken and force the concave recesses 220 inward towards each other. The contraction of the pelvic floor muscles 206 will also result in an elongation of the concave recesses 220 as the anchor protrusions 218 are forced apart.

Within the connecting body 212, the sensors 222 can be located. The sensors 222 can be an electro-mechanical strain-gauge sensor array, an array of resistive sensors, or a combination thereof. It is contemplated that the sensors 222 can be located entirely within the connecting body 212 or can extend from within the connecting body 212 partially into the bulbous body 210.

As depicted, the sensors 222 can be arranged within the insertable body 102 and are depicted located laterally near the surface 208 of the insertable body 102. The pelvic floor muscles 206 are depicted laterally surrounding the sensors 222 when inserted. The sensors 222 can detect the contractions of the pelvic floor muscles 206 in many ways.

The sensors 222 can detect the separation of the anchor protrusions 218 elongating the concave recesses 220. The sensors 222 can further detect the separation between the connecting body 212, the tail 104, and the bulbous body 210 during a contraction of the pelvic floor muscles 206.

The sensors 222 can further detect movement of the pelvic floor muscles 206 on the surface 208 of the insertable body 102 when the sensors 222 are located on or just under the surface 208 of the insertable body 102. The sensors 222 can further detect pressure exerted on the insertable body 102 during the contractions of the pelvic floor muscles 206. The sensors 222 can yet further detect the amount of surface contact between the pelvic floor muscles 206 and the surface 208 of the insertable body 102 when the sensors 222 are located on or just under the surface 208 of the insertable body 102.

Figure 4:
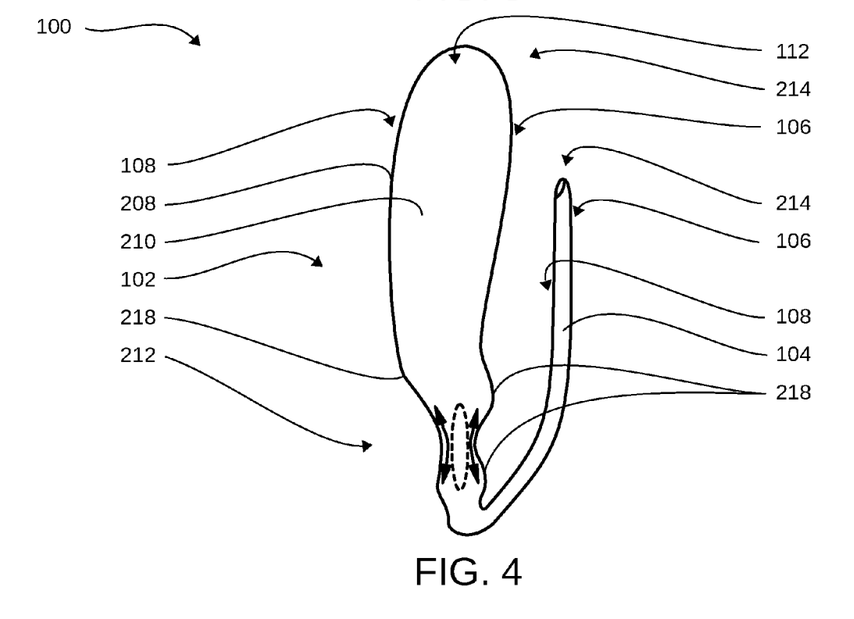
FIG. 4 is a side view of the Kegel health system of FIG. 1.

Referring now to FIG. 4, therein is shown a side view of the Kegel system 100 of FIG. 1. The Kegel system 100 is shown with the bulbous body 210 of the insertable body 102 extending from the connecting body 212 and the connecting body 212 connecting the tail 104 with the bulbous body 210.

The insertable body 102 is shown with the surface 208 of the back portion 108 being smooth and extending in a smooth convex shape from the anchor protrusions 218 of the connecting body 212 to the top portion 214 of the insertable body 102. The front portion 106 of the bulbous body 210 is shown curving back from the anchor protrusions 218 with a concave shape toward the back portion 108, then curving in a convex shape outward from the medial portions 112 before being in a dome shape near the top portion 214.

It is contemplated that the bulbous body 210 can extend three and one quarter inches from near the connecting body 212 to the top portion 214 of the insertable body 102. The connecting body 212 is contemplated to extend three quarters of an inch from the bulbous body 210 to the tail 104.

The tail 104 of the Kegel system 100 in FIG. 4 is shown angled closer to the insertable body 102 while the tail 104 of FIG. 2 is shown angled further from the insertable body 102. The tail 104 of FIG. 2 is shown bent or deformed outward away from the front portion 106 of the insertable body 102 while in the inserted phase and then returns to its rest state, as shown in FIG. 4, when not inserted.

The tail 104 can be seen in the rest state to extend out away from the connecting body 212 at a forty-five degree angle. The tail 104 can then include a curve allowing the top portion 214 of the tail 104 to extend vertically upward substantially parallel to the insertable body 102.

Figure 5:
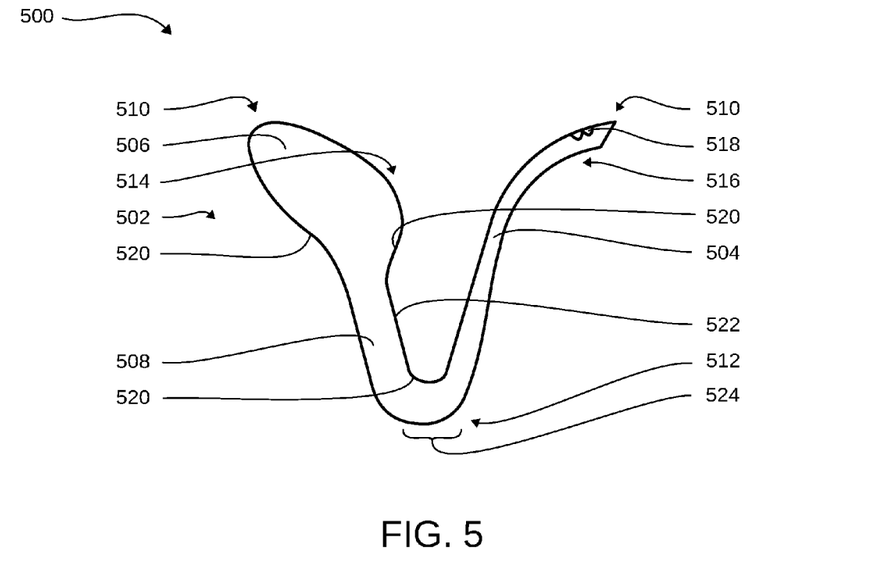
FIG. 5 is a side view of the Kegel health system in a second embodiment.

Referring now to FIG. 5, therein is shown a side view of the Kegel health system 500 in a second embodiment. The Kegel system 500 is similar to the Kegel system 100 of FIG. 1 in most respects including the communication with the external device 114 using the antennas 230 of FIG. 2, utilization of the sensor data 224 of FIG. 2 within the control unit 226 of FIG. 2, and providing the biofeedback utilizing the biofeedback unit 228 of FIG. 2.

The Kegel system 500, however, can differ from the Kegel system 100 in other respects. The Kegel health system 500 can include an insertable body 502 coupled to a tail 504.

The insertable body 502 can be comprised of two portions including a bulbous body 506 and a connecting body 508. The bulbous body 506 is depicted near a top portion 510 of the insertable body 502 while the connecting body 508 is depicted near a bottom portion 512 of the insertable body 502.

The bulbous body 506 can be angled back away from the tail 504 and extend downward from the top portion 510 of the insertable body 502 and terminate at the connecting body 508. The bulbous body 506 can extend at a forty five degree angle from the connecting body 508. The connecting body 508 can extend upward from the bottom portion 512 of the insertable body 502 and terminate at the bulbous body 506.

The tail 504 can extend from the bottom portion 512 of the insertable body 502 and can be in direct contact with the connecting body 508. The tail 504 is depicted extending outward away from a front portion 514 of the insertable body 502.

It is contemplated that the tail 504 would remain external to the user 202 of FIG. 2 while in use. The tail 504 is depicted including a curved extension 516 that can curve out away from the bulbous body 506.

The curved extension 516 can function as a handle while in an inserted phase of operation and can also extend out away from the user 202 so that the user 202 can see the curved extension 516 at the top portion 510 of the tail 504. The curved extension 516 can include LED indicators 518.

The LED indicators 518 can provide feedback to the user 202 during a contraction of the pelvic floor muscles 206 of FIG. 2. For example, it is contemplated that the LED indicators 518 can become brighter as a contraction of the pelvic floor muscles 206 intensifies or can flash faster as the contraction of the pelvic floor muscles 206 intensifies.

The tail 504 can be a wide flat tail having a width of five-eighths of an inch and a thickness of one-fourth of an inch. The LED indicators 518 can be positioned on the tail 504 so that the LED indicator 518 can be seen when the user 202 is in a seated position and the Kegel system 500 is in an inserted phase of operation.

The bottom portions 512 of the connecting body 508 can form a "J" shape to anchor the Kegel system 500 in the proper position relative to the pelvic floor muscles 206 and the pelvic floor 204 of FIG. 2 of the user 202. The tail 504 can extend up at an angle from the connecting body 508 and curve outward away from the insertable body 502 for the curved extension 516 near the top portion 510 of the tail 504 so that the top portion 510 of the tail 504 extends at roughly a forty-five degree angle away from the bulbous body 506.

The insertable body 502 is further depicted including anchor protrusions 520. The anchor protrusions 520 can be located on the insertable body 502 above and below the pelvic floor muscles 206.

The anchor protrusions 520 can be seen on either end of the connecting body 508. For instance the anchor protrusions 520 near the back portion 512 of the connecting body 508 can extend below the pelvic floor 204 when inserted in the user 202 while the anchor protrusions 520 near the top of the connecting body 508 can extend above the pelvic floor muscles 206 so that the pelvic floor muscles 206 rest entirely between the anchor protrusions 520.

The anchor protrusions 520 can extend laterally outward from the connecting body 508. The connecting body 508 itself can be seen to be provided in a straight configuration having straight sides 522 extending between the anchor protrusions 520. The anchor protrusions 520 and the straight sides 522 can be formed within the surface of the connecting body 508.

The top and bottom of the pelvic floor muscles 206 can be entirely between the anchor protrusions 520. The pelvic floor muscles 206 can further be in direct contact with portions of the straight sides 522 during use.

It is contemplated that when the pelvic floor muscles 206 contract, the pelvic floor muscles 206 will thicken and cover more surface area on the straight sides 522. During a contraction of the pelvic floor muscles 206, the pelvic floor muscles 206 will further exert an inward force towards each other squeezing the straight sides 522 together, as the contraction intensifies the amount of vertical surface area squeezed by the pelvic floor muscles 206 will increase.

Within the connecting body 508, sensors can be located. The sensors are contemplated to be the sensors 222 of FIG. 2 and can be an electro-mechanical strain-gauge sensor array, an array of resistive sensors, or a combination thereof. It is contemplated that the sensors 222 can be located entirely within the connecting body 508 and can detect the amount of pressure from the pelvic floor muscles 206 at multiple points along the straight sides 522 before, during, and after a contraction of the pelvic floor muscles 206.

Alternatively the sensors 222 can detect the type, position, and area of contact of the pelvic floor muscles 206 along the straight sides 522. The sensors 222 can output the sensor data 224 of FIG. 2 to a control unit such as the control unit 226 of FIG. 2. The sensor data 224 can be data sensed before, during, in between, and after contractions of the pelvic floor muscles 206.

The sensors 222 detect and digitize the evenness, pressure, frequency, number, intensity, speed, and direction of the contractions of the pelvic floor muscles 206. The sensors 222 can further determine whether the pelvic floor muscles 206 are contracting an even manner, that is: to what degree the pelvic floor muscles 206 thicken at various points around the connecting body 508.

It is contemplated that the tail 504 can be in direct contact with the connecting body 508 and can be coupled to the connecting body with a hinge 524. The hinge 524 can be an area that allows the tail 504 to pivot away from the insertable body 502 when inserted into the user 202.

Figure 6:
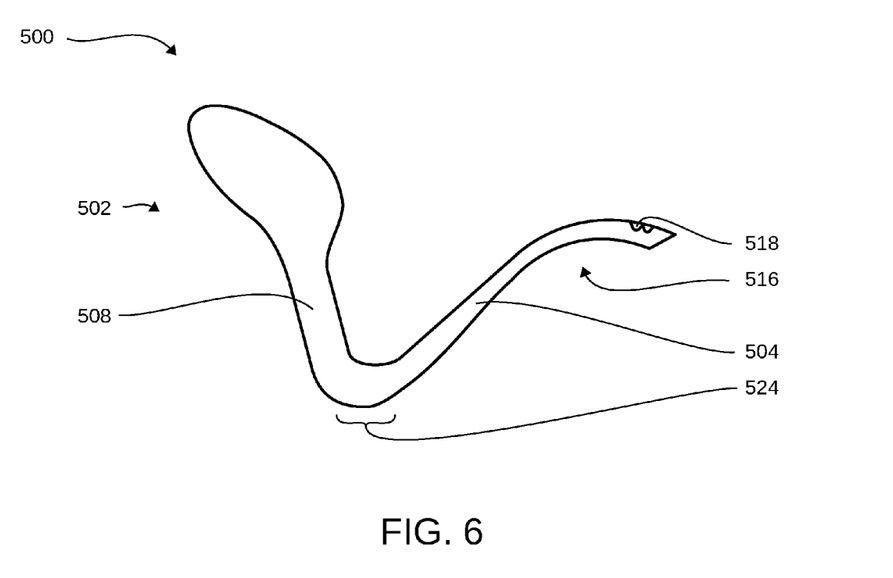
FIG. 6 is the Kegel health system of FIG. 5 in an inserted phase of operation.

Referring now to FIG. 6, therein is shown the Kegel health system 500 of FIG. 5 in an inserted phase of operation. The Kegel system 500 can be inserted into the user 202 of FIG. 2 and can extend above and below the pelvic floor 204 of FIG. 2 and the pelvic floor muscles 206 of FIG. 2.

The tail 504 can be completely external to the user 202 when in the inserted phase of operation. The tail 504 can be seen coupled to the connecting body with the hinge 524.

The hinge 524 is depicted allowing the tail 504 to pivot away from the insertable body 502 when inserted into the user 202. The tail can extend laterally out away from the insertable body 502 at a forty-five degree angle from the connecting body 508 when hinging from the hinge 524.

The curved extension 516 of the tail 504 is depicted curving past a horizontal plane. It is contemplated that the curved extension 516 can curve out away from the user 202 and allow the user 202 to see the LED indicator 518 near the top portion 510 of the tail 504 when the user 202 is in a sitting position.

Figure 7:
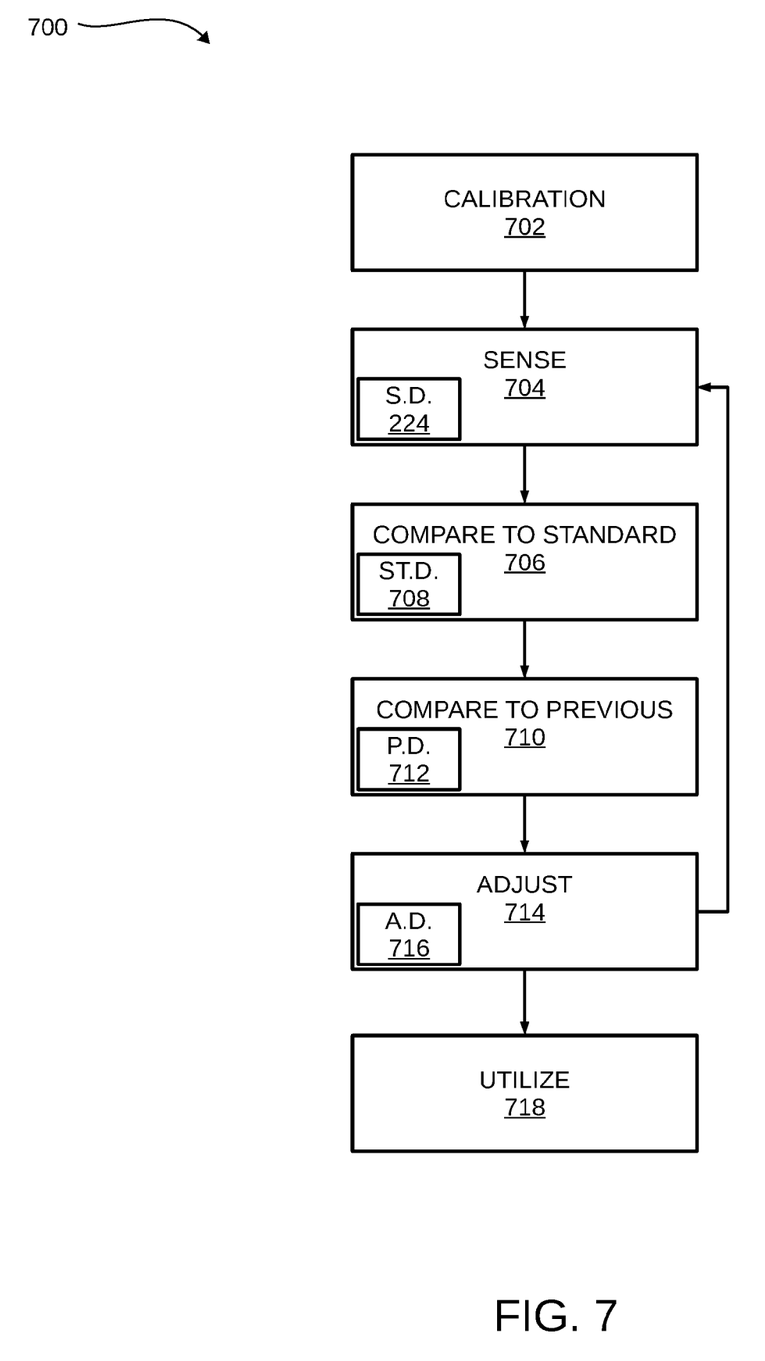
FIG. 7 is an operations control flow for both of the embodiments of the Kegel health system.

Referring now to FIG. 7, therein is shown an operations control flow 700 for both embodiments of the Kegel system; however, for ease of description the operations control flow 700 will be described with reference to the Kegel system 100 of FIG. 1. It will be understood by those having ordinary skill in the art that the operations control flow 700 could apply identically to the Kegel system 500 of FIG. 5.

The operations control flow 700 is shown setting forth contemplated steps that can be executed on the external device 114 of FIG. 1, on the control unit 226 of FIG. 2 within the insertable body 102 of FIG. 1, or a combination thereof. When executed on the control unit 226, the steps can be executed by a processor and information or data stored in memory and transmitted by the antennas 230 of FIG. 2.

It is contemplated that the Kegel system 100 can first execute a calibration step 702. During the calibration step 702 the sensors 222 of FIG. 2 can be adjusted and calibrated to ensure the sensors 222 are correctly detecting evenness, pressure, frequency, number, intensity, speed, and direction of the contractions of the pelvic floor muscles 206 of FIG. 2.

After the calibration step 702 a sense step 704 can collect the sensor data 224. It is contemplated that the sense step 704 can be executed before, during, after, and between contractions of the pelvic floor muscles 206.

Once the sensor data 224 is collected in the sense step 704, the sensor data 224 can be compared during a standards comparison step 706. The standards comparison step 706 can compare the sensor data 224 to standards data 708.

The standards data 708 can be the type of data expected to be generated by the sensors 222 during a standard type of contraction of the pelvic floor muscles 206. The standard type of contraction can be a general or average contraction for the general population.

The standards comparison step 706 can determine how closely the sensor data 224 relates to the standards data 708 to identify the evenness, pressure, frequency, number, intensity, speed, and direction of the contractions of the user 202 of FIG. 2. It is contemplated that Fourier transforms of the sensor data 224 and the standards data 708 can be compared during the standards comparison step 706 to determine the similarity of the sensor data 224 and the standards data 708. It is further contemplated that spectrograms of the sensor data 224 and the standards data 708 can be compared during the standards comparison step 706 to determine the similarity of the sensor data 224 and the standards data 708.

Once the sensor data 224 is compared to the standards data 708 in the standards comparison step 706, the sensor data 224 can be compared during a previous data comparison step 710. The previous data comparison step 710 can compare the sensor data 224 to previous data 712.

The previous data 712 can be the sensor data 224 captured or sensed by the sensors 222 during previously executed sense steps 704. The previous data 712 can include the sensor data 224 of previous contractions of the pelvic floor muscles 206 or averages of the sensor data 224 for previous contractions of the pelvic floor muscles 206.

The previous data comparison step 710 can determine how closely the sensor data 224 relates to the previous data 712 to identify the evenness, pressure, frequency, number, intensity, speed, and direction of the contractions of the user 202. It is contemplated that Fourier transforms of the sensor data 224 and the previous data 712 can be compared during the previous data comparison step 710 to determine the similarity of the sensor data 224 and the previous data 712.

It is further contemplated that spectrograms of the sensor data 224 and the previous data 712 can be compared during the previous data comparison step 710 to determine the similarity of the sensor data 224 and the previous data 712. Once the sensor data 224 is compared to the standards data 708 during the standards comparison step 706 and the sensor data 224 is compared to the previous data 712 during the previous data comparison step 710, the sensor data 224 can be adjusted during an adjustment step 714.

The adjustment step 714 can adjust the sensor data 224 to provide adjusted data 716. The adjusted data 716 can be the sensor data 224 collected by the sensors 222 that has been adjusted based on the differences and similarities detected during the standards comparison step 706 and the previous data comparison step 710.

The adjusted data 716 can be data that matches more closely to, or more accurately represents, the actual evenness, pressure, frequency, number, intensity, speed, and direction of contractions of the pelvic floor muscles 206 than does the sensor data 224 originally collected. Once the adjustment step 714 has provided the adjusted data 716, the Kegel system 100 can again execute the sense step 704 and detect the sensor data 224 from the sensors 222.

The Kegel system 100 can execute a data utilization step 718 after the adjustment step 714 in parallel with the execution of the sense step 704. Executing the data utilization step 718 in parallel with the sense step 704 can allow the Kegel system 100 to provide real time monitoring and feedback of contractions of the pelvic floor muscles 206 to the user 202.

Figure 8:
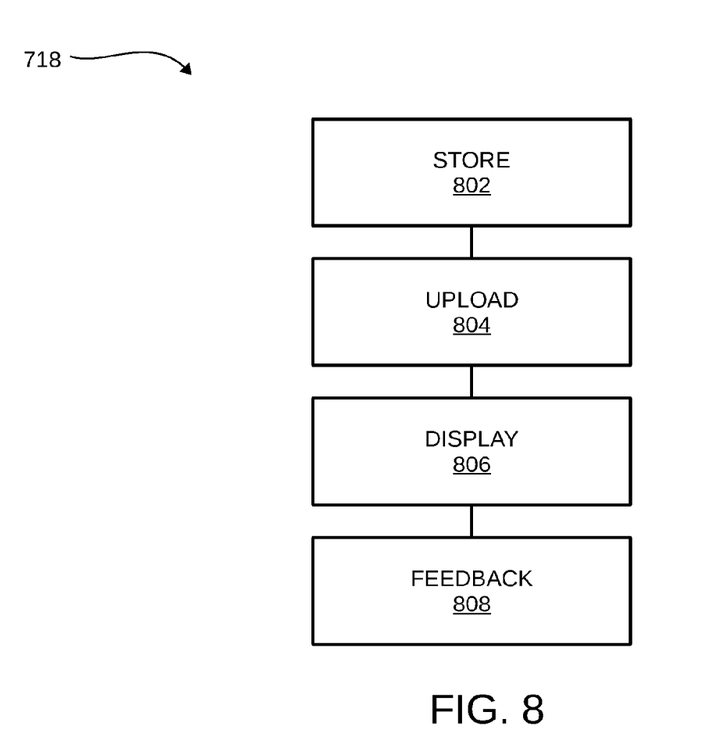
FIG. 8 is a control flow for the data utilization step of FIG. 7.

Referring now to FIG. 8, therein is shown a control flow for the data utilization step 718 of FIG. 7. The data utilization step 718 can begin with a store step 802. During the store step 802, the adjusted data 716 of FIG. 7 and the sensor data 224 of FIG. 2 can be stored in memory within the control unit 226 of FIG. 2.

In cases where the adjustment step 714 of FIG. 7 is executed on the external device 114 of FIG. 1, the adjusted data 716 can be stored within the external device 114 during the store step 802. Once the store step 802 stores the adjusted data 716, an upload step 804 can be executed.

During the upload step 804, the adjusted data 716 and the sensor data 224 can be transmitted by the wireless signal 116 of FIG. 1 from the antennas 230 of FIG. 2 within the tail 104 of FIG. 1. The adjusted data 716 can be received by the external device 114 during the upload step 804.

It is contemplated that the upload step 804 could be skipped in cases where the adjustment step 714 is executed on the external device 114. Once the external device 114 has the adjusted data 716 and the sensor data 224, a display step 806 can be executed.

During the display step 806, the adjusted data 716 can be processed for proper display on the display 120 of FIG. 1. For example, the adjusted data 716 can be processed so that it could be displayed graphically as an avatar or plot on the graphics 122 of FIG. 1. As a further illustrative example, the adjusted data 716 can be processed so that it could be displayed as the written information 124 of FIG. 1. A feedback step 808 can also be executed after the display step 806. It is contemplated that the feedback step 808 can be executed in parallel with the display step 806 or even before the display step 806.

The feedback step 808 can process the adjusted data 716 and compare the adjusted data 716 with a desired evenness, pressure, frequency, number, intensity, speed, and direction of contractions for the pelvic floor muscles 206 of FIG. 2. The feedback step 808 can instruct the biofeedback unit 228 of FIG. 2 within the insertable body 102 of FIG. 1 to provide vibrations to the user 202 of FIG. 2. The feedback step 808 can further be used to provide audio and visual feedback to the user 202 with the external device 114.

Figure 9:
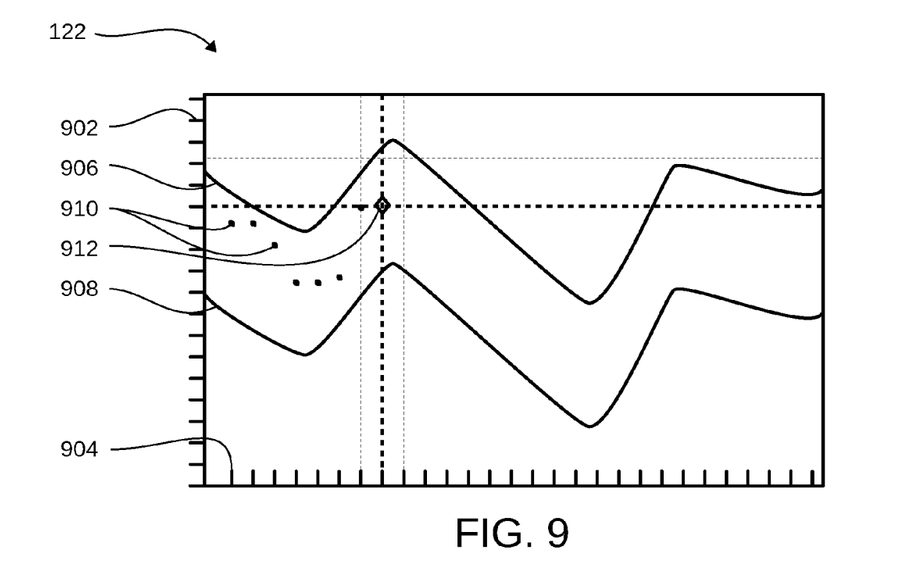
FIG. 9 are graphics for the display of FIG. 1.

Referring now to FIG. 9, therein are shown the graphics 122 for the display 120 of FIG. 1. The adjusted data 716 of FIG. 7 is depicted in a graphical form and displayed on the display 120 of the external device 114 of FIG. 1.

The graphics 122 of the display 120 is shown to include a graph measuring the intensity 902 of contractions of the pelvic floor muscles 206 of FIG. 2 on the vertical left side and time 904 along the horizontal bottom.

The display 120 is shown having a moving upper bound 906 and a moving lower bound 908. The moving upper bound 906 and the moving lower bound 908 can guide the user 202 of FIG. 2 to produce contractions of the pelvic floor muscles 206 of a specific intensity as the moving upper bound 906 and the moving lower bound 908 move across the graphics 122 of the display 120.

Further the display 120 is shown having dots 910 plotted within the moving upper bound 906 and the moving lower bound 908 that depict the adjusted data 716 from past contractions of the user 202. It is contemplated that as the moving upper bound 906 and the moving lower bound 908 move across the display 120 the dots 910 will maintain their position relative to the moving upper bound 906 and the moving lower bound 908.

Further the display 120 is shown having a current contraction marker 912 plotted within the moving upper bound 906 and the moving lower bound 908 that depict the adjusted data 716 from a current contraction of the user 202. The current contraction marker 912 can be positioned along further to the right of the dots 910 along the x-axis indicating that the current contraction marker 912 is detected later in time 904 than the dots 910.

It has been discovered that providing the graphics 122 including the dots 910, the current contraction marker 912, the moving upper bound 906, and the moving lower bound 908 incentivize the user 202 to hit or miss the graphic elements and thereby train the user 202 to more accurately control contractions of the pelvic floor muscles 206.

The intensity 902 can correspond to a percentage of intensity, that is a full contraction could be 100% while half of that intensity 902 could be 70% and can be displayed accordingly. The moving upper bound 906 and the moving lower bound 908 can guide the user 202 in producing a range of the intensity 902 of contractions for the pelvic floor muscles 206 and can direct the user 202 to hold the contraction at the specified intensity 902 for a predetermined amount of the time 904.

It is contemplated that the previous data 712 of FIG. 7 can be tracked to determine the progress that the user 202 makes in controlling and strengthening the pelvic floor muscles 206. It is further contemplated that the Kegel system 100 can be used to produce exercise programs according to the goals and to the stage of life of the user 202. It is contemplated that the exercise programs could be tailored for postpartum status, age, and general toning goals.

Thus, it has been discovered that the Kegel system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the Kegel system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. A method of operating a Kegel health system comprising:

inserting an insertable body into a user, the insertable body connected to a tail outside of the user, the insertable body including a bulbous body coupled to a connecting body, the bulbous body including a control unit, the connecting body coupled to the tail, the connecting body including sensors, and the connecting body configured to have pelvic floor muscles laterally surround the sensors based on the insertable body being inserted into the user;

sensing sensor data including sensing an evenness, a pressure, a frequency, a number, an intensity, a speed, and a direction of the contractions from the pelvic floor muscle with the sensors, the sensor data indicating the presence of contractions from the pelvic floor muscle of the user; and providing feedback to the user with graphics and written information displayed on an external device, the graphics and the written information indicating attributes of the contractions from the pelvic floor muscle.

2. The method of claim 1 further comprising transmitting data of the contractions from the pelvic floor muscle to the external device with an antenna within the tail.

3. The method of claim 1 wherein displaying the graphics and the written information to the user includes depicting an intensity of the contractions from the pelvic floor muscles on a display of the external device.

4. The method of claim 1 further comprising:
compare the sensor data with previous data collected by the sensors;
comparing the sensor data to standards data; and
calculating adjusted data based on the comparison of the sensor data to the standards data and the previous data.

5. The method of claim 1 wherein displaying the graphics includes displaying a moving upper bound, a moving lower bound, dots, and a current contraction marker, the moving upper bound and the moving lower bound indicating a changing window of intensity required for the contractions, the dots indicating the intensity of previous contractions by the user, and the current contraction marker indicating the intensity for the most recent contraction of the user.

6. The method of claim 1 wherein providing the feedback further includes providing biofeedback with vibration from within the insertable body, providing visual feedback from an LED indicator located on the tail, or a combination thereof.

7. A non-transitory computer readable medium, useful in association with a processor, including instructions configured to:

sense sensor data including an evenness, a pressure, a frequency, a number, an intensity, a speed, and a direction of the contractions from the pelvic floor muscle with the sensors within an insertable body inserted into a user, the insertable body connected to a tail outside of the user, the insertable body including a bulbous body coupled to a connecting body, the bulbous body including a control unit, the connecting body coupled to the tail, the connecting body including sensors, the connecting body configured to have pelvic floor muscles laterally surround the sensors based on the insertable body being inserted into the user, and the sensor data indicating the presence of contractions from the pelvic floor muscle of the user; and providing feedback to the user with graphics and written information displayed on an external device, the graphics and the written information indicating attributes of the contractions from the pelvic floor muscle.

8. The computer readable medium of claim 7 further comprising instructions configured to transmit data of the contractions from the pelvic floor muscle to the external device with an antenna within the tail.

9. The computer readable medium of claim 7 wherein the instructions configured to display the graphics and the written information further includes instructions configured to depict an intensity of the contractions from the pelvic floor muscles on a display of the external device.

10. The computer readable medium of claim 7 further comprising instructions configured to:
compare the sensor data with previous data collected by the sensors;
compare the sensor data to standards data; and
calculate adjusted data based on the comparison of the sensor data to the standards data and the previous data.

11. The computer readable medium of claim 7 wherein the instructions configured to display the graphics and the written information further includes instructions configured to display a moving upper bound, a moving lower bound, dots, and a current contraction marker, the moving upper bound and the moving lower bound indicating a changing window of intensity required for the contractions, the dots indicating the intensity of previous contractions by the user, and the current contraction marker indicating the intensity for the most recent contraction of the user.

12. The computer readable medium of claim 7 wherein the instructions configured to provide the feedback further includes instructions configured to provide biofeedback with vibration from within the insertable body, provide visual feedback from an LED indicator located on the tail, or a combination thereof.

13. A Kegel health system comprising:
an insertable body configured to be inserted into a user, the insertable body connected to a tail configured to be outside of the user, the insertable body including a bulbous body coupled to a connecting body, the bulbous body including a control unit, the connecting body coupled to the tail, the connecting body including sensors, the connecting body configured to have pelvic floor muscles laterally surround the sensors based on the insertable body being inserted into the user, and the sensors configured to sense sensor data including an evenness, a pressure, a frequency, a number, an intensity, a speed, and a direction of the contractions from the pelvic floor muscle, the sensor data indicating the presence of contractions from the pelvic floor muscle of the user; and an external device configured to provide feedback to the user with graphics and written information displayed on the external device, the graphics and the written information indicating the attributes of the contractions from the pelvic floor muscle.

14. The system of claim 13 further comprising an antenna within the tail for transmitting data of the contractions from the pelvic floor muscle to the external device.

15. The system of claim 13 wherein the external device further includes a display configured to depicting an intensity of the contractions from the pelvic floor muscles.

16. The system of claim 13 wherein the control unit, the external device, or a combination thereof is configured to:
compare the sensor data with previous data collected by the sensors;
compare the sensor data to standards data; and
calculate adjusted data based on the comparison of the sensor data to the standards data and the previous data.

17. The system of claim 13 wherein the external device further includes a display configured to display a moving upper bound, a moving lower bound, dots, and a current contraction marker, the moving upper bound and the moving lower bound indicating a changing window of intensity required for the contractions, the dots indicating the intensity of previous contractions by the user, and the current contraction marker indicating the intensity for the most recent contraction of the user.

* * * * *

UNITED STATES PATENT AND TRADEMARK OFFICE
CERTIFICATE OF CORRECTION

PATENT NO. : 9,855,462 B2
APPLICATION NO. : 15/079807
DATED : January 2, 2018
INVENTOR(S) : Julia Rose

Page 1 of 2

It is certified that error appears in the above-identified patent and that said Letters Patent is hereby corrected as shown below:

In the Claims

On Column 13:
Line 8, (Line 14 of Claim 1), delete "of the contractions" and replace with --of contractions--;
Lines 8-9, (Lines 14-15 of Claim 1), delete "the pelvic floor muscle" and replace with --the pelvic floor muscles--;
Lines 9-10, (Lines 15-16 of Claim 1), delete "the presence" and replace with --a presence--;
Line 10, (Line 16 of Claim 1), delete "of contractions" and replace with --of the contractions--;
Line 10, (Line 16 of Claim 1), delete "the pelvic floor muscle" and replace with --the pelvic floor muscles--;
Line 15, (Line 21 of Claim 1), delete "the pelvic floor muscle." and replace with --the pelvic floor muscles.--;
Line 17, (Line 2 of Claim 2), delete "the pelvic floor muscle" and replace with --the pelvic floor muscles--;
Lines 21-22, (Lines 2-3 of Claim 3), delete "an intensity" and replace with --the intensity--;
Line 28, (Line 5 of Claim 4), delete "the comparison" and replace with --a comparison--;
Line 37, (Line 8 of Claim 5), delete "the most recent contraction" and replace with --a most recent contraction--;
Line 48, (Line 6 of Claim 7), delete "of the contractions" and replace with --of contractions--;
Lines 48-49, (Lines 6-7 of Claim 7), delete "from the pelvic floor muscle" and replace with --from pelvic floor muscles--;
Line 49, (Line 7 of Claim 7), delete "with the sensors" and replace with --with sensors--;
Lines 54-55, (Lines 12-13 of Claim 7), delete "including sensors," and replace with --including the sensors,--;
Lines 55-56, (Lines 13-14 of Claim 7), delete "have pelvic floor muscles" and replace with --have the pelvic floor muscles--;
Line 58, (Line 16 of Claim 7), delete "indicating the presence" and replace with --indicating a presence--;
Line 58, (Line 16 of Claim 7), delete "of contractions" and replace with --of the contractions--;

Signed and Sealed this
Thirtieth Day of June, 2020

Andrei Iancu
*Director of the United States Patent and Trademark Office*

Line 59, (Line 17 of Claim 7), delete "the pelvic floor muscle" and replace with --the pelvic floor muscles--;
Line 63, (Line 21 of Claim 7), delete "the pelvic floor muscle." and replace with --the pelvic floor muscles.--; and
Line 66, (Line 3 of Claim 8), delete "the pelvic floor muscle" and replace with --the pelvic floor muscles--.

On Column 14:
Line 4, (Line 4 of Claim 9), delete "an intensity" and replace with --the intensity--;
Line 11, (Line 6 of Claim 10), delete "the comparison" and replace with --a comparison--;
Line 22, (Line 10 of Claim 11), delete "the most recent contraction" and replace with --a most recent contraction--;
Line 41, (Line 13 of Claim 13), delete "of the contractions" and replace with --of contractions--;
Line 42, (Line 14 of Claim 13), delete "the pelvic floor muscle," and replace with --the pelvic floor muscles,--;
Lines 42-43, (Lines 14-15 of Claim 13), delete "the presence" and replace with --a presence--;
Line 43, (Line 15 of Claim 13), delete "of contractions" and replace with --of the contractions--;
Line 43, (Line 15 of Claim 13), delete "the pelvic floor muscle" and replace with --the pelvic floor muscles--;
Line 48, (Line 20 of Claim 13), delete "indicating the attributes" and replace with --indicating attributes--;
Line 49, (Line 21 of Claim 13), delete "the pelvic floor muscle." and replace with --the pelvic floor muscles.--;
Line 52, (Line 3 of Claim 14), delete "the pelvic floor muscle" and replace with --the pelvic floor muscles--;
Lines 54-55, (Lines 2-3 of Claim 15), delete "depicting an intensity" and replace with --depicting the intensity--; and
Line 61, (Line 6 of Claim 16), delete "the comparison" and replace with --a comparison--.

On Column 15:
Lines 3-4, (Lines 8-9 of Claim 17), delete "the most recent contraction" and replace with --a most recent contraction--.